(12) United States Patent
Trieu

(10) Patent No.: US 8,425,604 B2
(45) Date of Patent: Apr. 23, 2013

(54) SPINAL IMPLANT WITH ATTACHABLE BONE SECURING COMPONENT

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 93 days.

(21) Appl. No.: 13/010,569

(22) Filed: Jan. 20, 2011

(65) Prior Publication Data

US 2012/0191190 A1 Jul. 26, 2012

(51) Int. Cl.
*A61F 2/44* (2006.01)
(52) U.S. Cl.
USPC .............. 623/17.11; 623/17.16; 606/246; 606/248; 606/249
(58) Field of Classification Search .......... 606/246, 606/248, 249; 623/17.11–17.16
See application file for complete search history.

(56) References Cited

U.S. PATENT DOCUMENTS

2007/0043442 A1\* 2/2007 Abernathie et al. ....... 623/17.11

\* cited by examiner

*Primary Examiner* — Eduardo C Robert
*Assistant Examiner* — Christina Negrellirodriguez

(57) ABSTRACT

A spinal implant for insertion into an intervertebral disc space for intervertebral stabilization, the implant comprising a radiolucent polymer substrate coupled to a radiopaque and osseoconductive bone securing component which provides the implant with secure fixation between adjacent vertebrae. The implant's radiolucent, radiopaque and osseointegrative properties facilitate radiographic assessment of fusion across the disc space, assessment of osseointegration between vertebral endplates and osseointegration of the spinal implant to adjacent vertebral end plates. The implant comprises an implant substrate and a securing component coupled to the implant substrate. The implant preferably comprises a radiolucent polyetheretherketone (PEEK) substrate coupled to a radiopaque Titanium (Ti) or a titanium (Ti) alloy securing component, whereby the securing component is adjacent to the vertebral endplates when the implant is inserted in the disc space. The securing component comprises surface teeth or extension to secure the implant, within the intervertebral disc space to adjacent vertebrae.

20 Claims, 7 Drawing Sheets

SPINAL IMPLANT WITH ATTACHABLE BONE SECURING COMPONENT

BACKGROUND

The present application is directed to implants, devices and methods for stabilizing vertebral members, and more particularly, to intervertebral implants, devices and methods of use in replacing, in whole or in part, an intervertebral disc, a vertebral member, or a combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion of the spinal elements.

Various procedures include replacing a section of or an entire intervertebral disc, a section of or an entire vertebral member, or both. One or more spinal implants may be inserted to replace damaged discs and/or vertebral members. The implants are configured to be inserted into an intervertebral space and contact against adjacent vertebral members. The implants are intended to reduce or eliminate the pain and neurological deficit, and increase the range of motion.

The curvature of the spine and general shapes of the vertebral members may make it difficult for the implants to adequately contact the adjacent vertebral members or to position the adjacent vertebral members in a desired orientation. There is a need for spinal implants or devices configurable to match the spinal anatomy for secure contact and/or desired orientation of the spinal implants or devices implanted into an intervertebral disc space.

SUMMARY

The present application discloses a spinal implant for insertion into and positioning in an intervertebral disc space. The implant comprises an implant substrate comprising at least one attachment aspect and a securing component comprising at least one securing aspect. The securing component, via the securing aspect, is coupled to the implant substrate via the attachment aspect to thereby form the spinal implant. The securing component can comprises a plurality of extensions or teeth adapted to engage adjacent vertebrae when the implant is in positioned in the disc space. The securing component can be attached to the implant substrate at an upper or lower implant section or a lateral implant section. In a preferred embodiment, the implant has a radiolucent PEEK implant substrate and a radiopaque Titanium (Ti) or a titanium (Ti) alloy metallic securing component. Also, the securing component may further be coated with a Hydroxyapatite (HA) layer.

The present application also discloses a spinal implant for insertion into and positioning in an intervertebral disc space. The implant comprises a radiolucent implant substrate comprising at least one attachment aspect and a radiopaque securing component comprising at least one securing aspect and a plurality of extensions. The securing component, via the securing aspect, can be coupled to the implant substrate via the attachment aspect to thereby form the spinal implant, such that the plurality of extensions engage adjacent vertebrae when the implant is in positioned in the disc space. The securing component can be attached to the implant substrate at an upper or lower implant section or a lateral implant section.

There is further provided a spinal implant for insertion into an intervertebral disc space for intervertebral stabilization, the implant comprising a radiolucent polymer substrate coupled to a radiopaque and osseoconductive bone securing component which provides the spinal implant with secure fixation within the intervertebral disc space and adjacent vertebrae. The disclosed spinal implant includes radiolucent, radiopaque and osseointegrative properties that facilitate radiographic assessment of fusion across the disc space, assessment of osseointegration between vertebral endplates and osseointegration of the spinal implant to adjacent vertebral end plates.

The present application also discloses a biocompatible spinal implant for insertion into an intervertebral space between adjacent vertebral members. The implant imparts, distracts and restores desired disc space height in adjacent vertebral bodies when the implant is positioned in the intervertebral disc space and enables fusion of the adjacent vertebrae. The implant comprises a radiolucent polyetheretherketone (PEEK) polymer substrate coupled with a metallic bone securing component having surface teeth which enable the spinal implant to be securely positioned in the intervertebral disc space between adjacent vertebral endplates. In a preferred aspect, the bone securing component is preferably a titanium (Ti) material or a titanium (Ti) alloy.

The various aspects of the various embodiments may be used alone or in any combination, as is desired. Disclosed aspects or embodiments are discussed and depicted in the attached drawings and the description provided below.

DETAILED DESCRIPTION

The present disclosure is directed to intervertebral implants for spacing apart vertebral members. The present disclosure relates to medical devices such as spinal intervertebral implants implanted between adjacent vertebral bodies of a spinal column section, and methods of use. More particularly, to a spinal implant with a polymer substrate coupled to a securing component with the securing component having surface extensions, texture, teeth or serrations which enable the spinal implant to be securely positioned between adjacent vertebral endplates. The implant imparts, distracts and restores desired disc space height in adjacent vertebral body when the implant is positioned in the intervertebral disc space. The disclosed spinal implant includes radiolucent, radiopaque and osseointegrative properties that facilitate radiographic assessment of fusion across the disc space, assessment of osseointegration between vertebral endplates and implant surfaces, and osseointegration of the spinal implant to adjacent vertebral end plates. For purposes of promoting an understanding of the principles of the invention, reference will now be made to one or more embodiments or aspects, examples, drawing illustrations, and specific language will be used to describe the same. It will nevertheless be understood that the various described embodiments or aspects are only exemplary in nature and no limitation of the scope of the invention is thereby intended. Any alterations and further modifications in the described embodiments or aspects, and any further applications of the principles of the invention as described herein are contemplated as would normally occur to one skilled in the art to which the invention relates.

Figure 1:
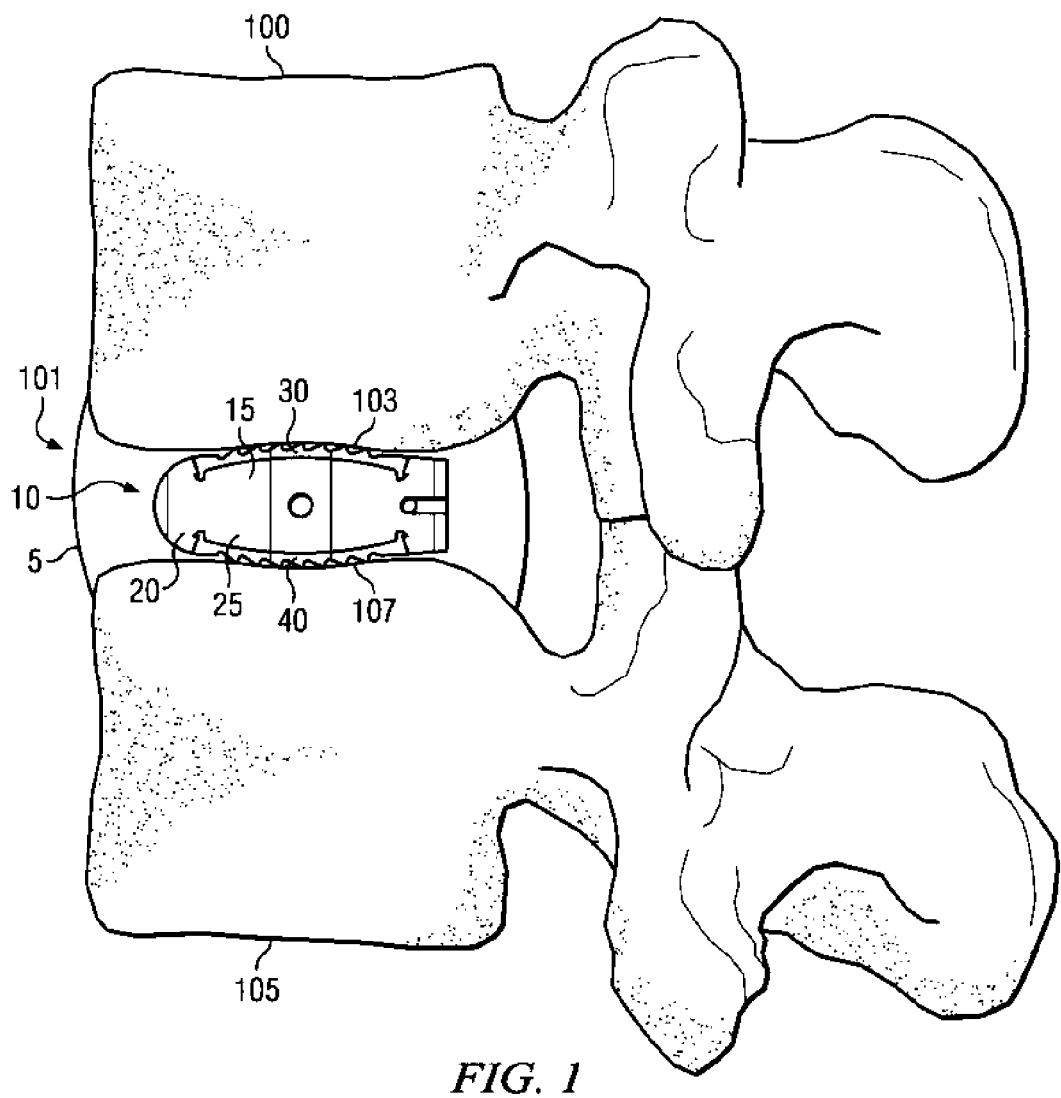
FIG. 1 is sagittal plane view of an implant according to one embodiment of the present disclosure positioned in an intervertebral space between vertebral members.

FIG. 1 illustrates a sagittal plane view of vertebral joint section or motion segment of a vertebral column. A spinal implant or device 10 is positioned in an intervertebral disc space 101 between adjacent vertebral members 100 and 105. The upper and lower vertebral bodies 100 and 105 include respective end plates 103 and 107. An intervertebral disc space 101 is located between the endplates 103 and 107. An intervertebral disc 5 is located in the intervertebral disc space 101 between the adjacent endplates 103 and 107 and around the periphery of the disc space 101. The intervertebral disc 5 is comprised of an annulus fibrosus or annulus which surrounds a nucleus pulposus.

FIG. 1 further depicts a spinal implant, spacer or device 10 with attachable securing components 80 and 81 positioned in the intervertebral disc space 101. The spinal implant 10 can be used to promote fusion or preserve motion between adjacent vertebral bodies 100 and 105, depending on the specific shape or configuration of the implant used in a surgical procedure.

FIG. 1 depicts an implantation technique where the spinal implant 10 has been delivered to the intervertebral disc space 101, for example via a known surgical technique such as a posterior lumbar interbody fusion (PLIF) approach and procedure. Such a spinal implant PLIF procedure and approach is a well known surgical implant procedure and delivery approach for delivery and insertion of a spinal implant 10 into a desired or selected intervertebral disc space 101. Those of skill in the art will recognize that the spinal implant 10 could also be delivered and inserted in the disc space 101 so as to have different orientations and positions in the disc space 101 between the adjacent vertebrae 100 and 105. For example using other well known surgical approaches, including, anterior, posterior, direct lateral, translateral, posterolateral, anterolateral or any other suitable oblique direction desired or required by a surgeon or medical application. The spinal implant 10 could also be delivered and inserted in the disc space 101 using other well known surgical procedures and techniques, including among others, anterior lumbar interbody fusion (ALIF), direct lateral lumbar interbody fusion (DLIF), transforaminal lumbar interbody fusion (TLIF) or other known surgical procedures or techniques desired or required by a surgeon or medical application. Further, those of skill in the art will also recognize that a spinal implant 10 may be delivered and inserted through known surgical techniques and procedures via open, mini-open, minimal access spinal technologies (MAST) or other minimally invasive surgical (MIS) techniques. Moreover, delivery and insertion of the present spinal implant 10 is contemplated through the use of typical and existing instruments presently known and used in existing surgical approached, procedures and techniques.

Figure 2:
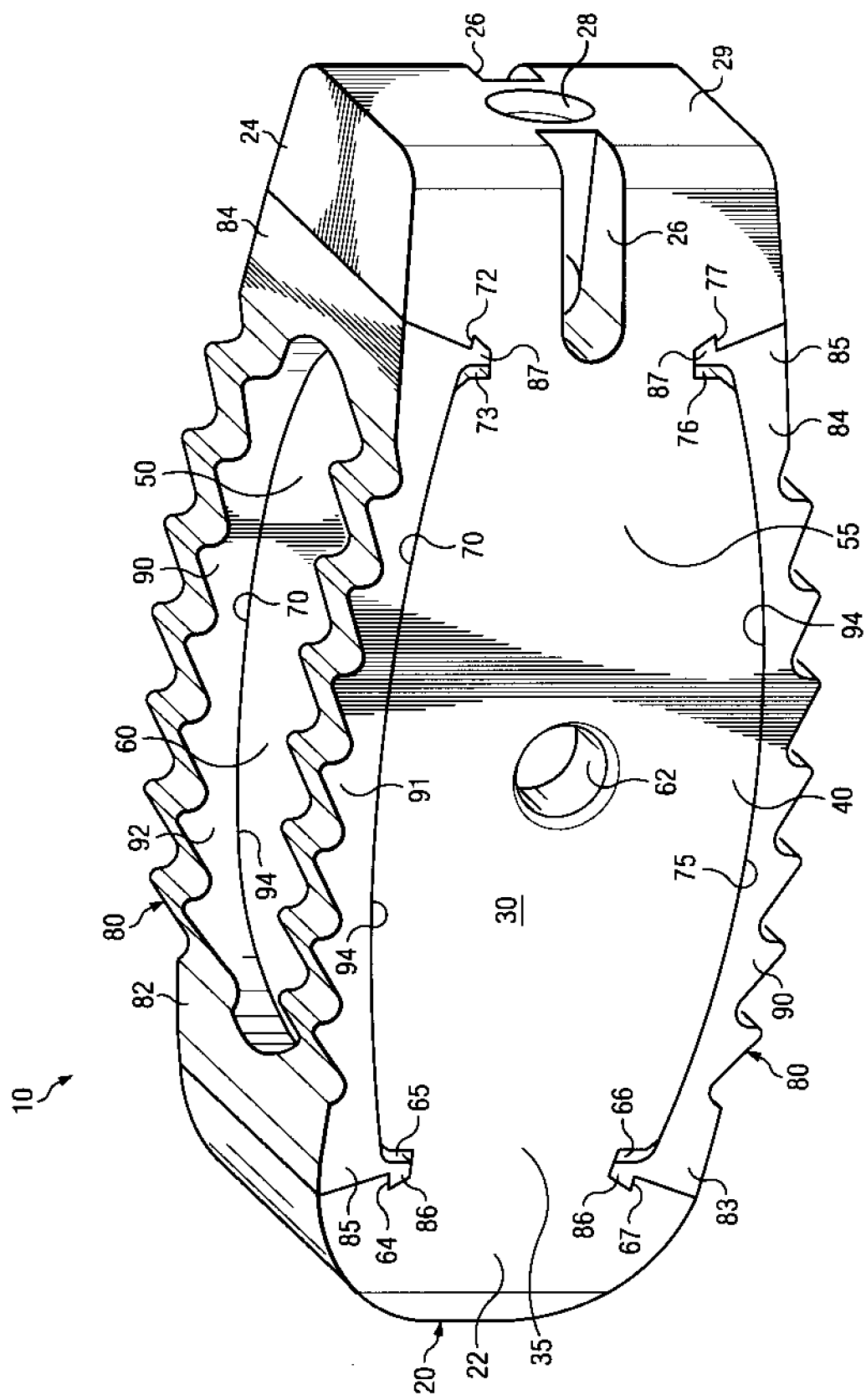
FIG. 2 is a perspective view of an implant according to one embodiment of the present disclosure.
Figure 3:
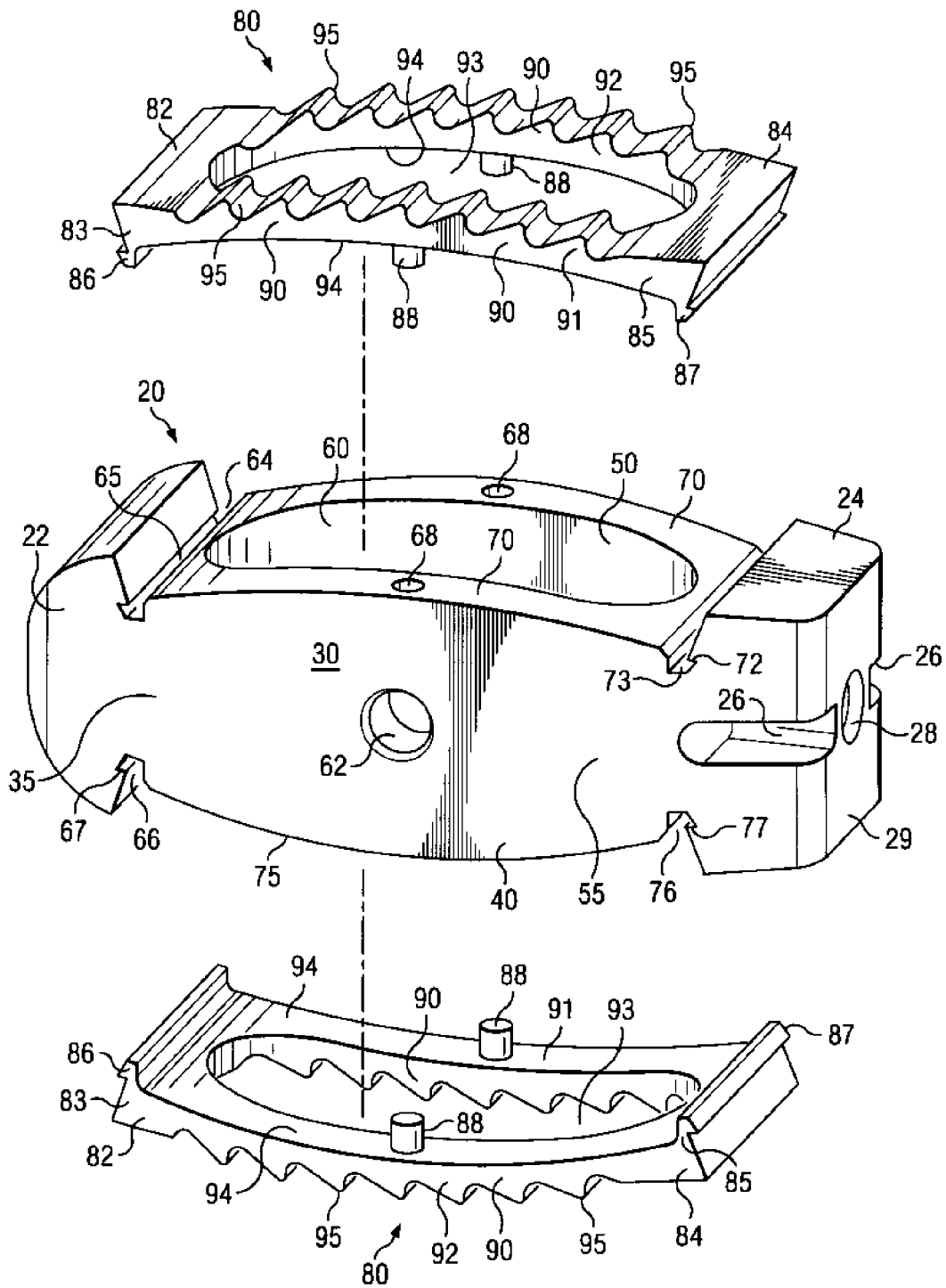
FIG. 3 is an exploded perspective view of the implant of FIG. 2.
Figure 4:
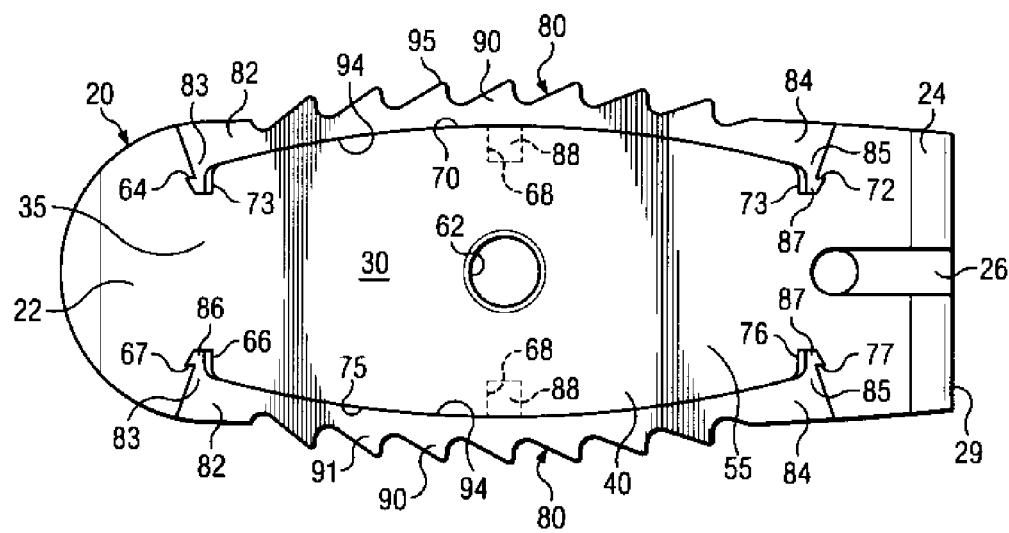
FIG. 4 is a side view of the implant of FIG. 2.
Figure 5:
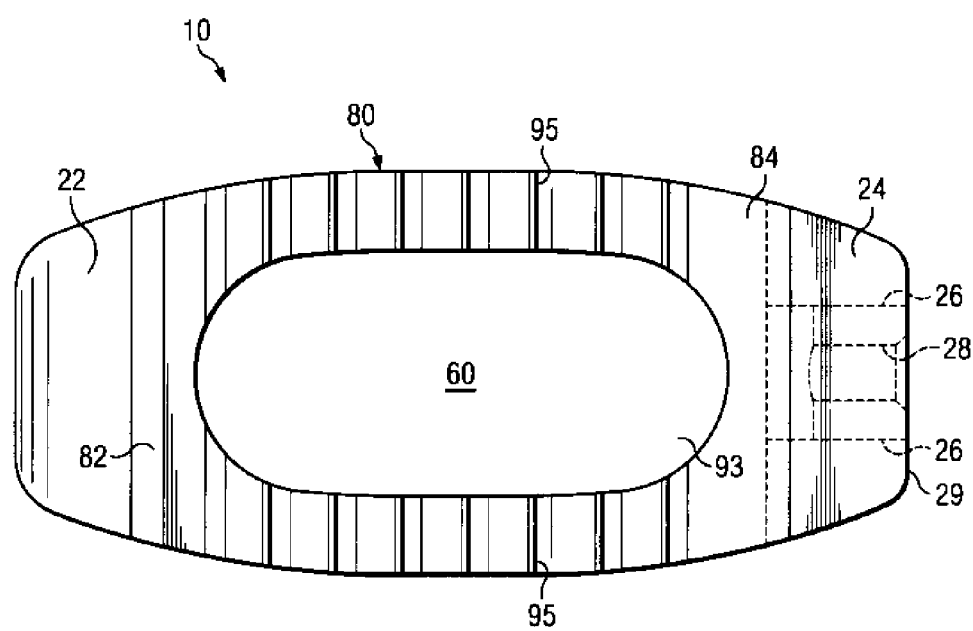
FIG. 5 is a top view of the implant of FIG. 2.

FIGS. 2-5 illustrate a spinal implant 10 according to a preferred aspect of the present disclosure. FIG. 2 is perspective view of the preferred spinal implant 10. FIG. 3 is an exploded perspective view of the spinal implant 10 of FIG. 2. FIGS. 4 and 5 are side and top views of the preferred spinal implant 10 of FIG. 2. The implant 10 comprises an implant body or substrate 20 and first and second securing components 80 and 81 which are attached to the implant body 20. In the embodiment shown in FIG. 1, a first securing component 80 of the spinal implant 10 is secured or attached to the implant's upper or cephalad section or surface 70, and a second securing component 81 is secured or attached to the implant's lower or caudal section or surface 75. In the preferred aspect of the spinal implant 10, the first and second securing components 80 or 81 are respectively secured or attached to upper and lower implant sections 70 and 75. Those of skill in the art will recognize that if desired or needed by a surgeon or a particular medical application, the securing components 80 and 81 could instead be secured or attached to first and second lateral implant sections 270 and 275, for example as shown in FIGS. 6-9. Further, those of skill in the art will recognize that that instead of two securing components, a spinal implant may have one or more securing components secured or attached to the implant body or substrate 20 depending on the selection or requirement of a surgeon or medical procedure or application. Additionally, the spinal implant 10 can comprise a shape, configuration or size that may be needed by a surgeon or a spinal implant procedure or application. FIGS. 2-5 show one such spinal implant embodiment.

In a preferred aspect, the spinal implant 10 comprises a substrate 20 and at least one bone securing component 80 or 81. The substrate 20 comprises a leading end 22 which has a substantially curved or rounded surface to permit the implant body 10 to distract collapsed or semi-collapsed adjacent vertebral bodies 100 and 105 when the implant 10 is introduced or inserted into a disc space 101. The implant 10 also includes a rear end 24 with a recess section 26 and orifice 28 extending inwardly in a direction from a rear end wall 29 toward the implant's leading end 22. The recess section 26 and orifice 28 provide a means to attach an instrument (not show) to grasp, attach to and manipulate the insertion and orientation of the spinal implant 10 as the implant 10 is delivered to a selected or desired disc space 101.

The spinal implant substrate 20 further comprises a substrate connecting or attachment section 30 between the leading and rear end 22 and 24. The substrate attachment section 30 comprises a leading connector section 35 adjacent the leading end 22, a rear connector section 55 adjacent the rear end 24, and first and second lateral sidewalls 40 and 50 between the leading connector section 32 and rear connector section 55. In this embodiment, the first and second lateral sidewalls 40 and 50, the leading connector section 35 and the rear connector section 55 are configured such that they define an implant substrate aperture 60. The present embodiment further includes first and second lateral wall substrate apertures 62. The implant apertures 60 and 62 permit the insertion of a graft material which assists in promoting fusion 100 and 105 of the adjacent vertebrae at the disc space 101 where the implant 10 is inserted. The graft material may be composed of any type of material that has the ability to promote, enhance and/or accelerate the bone growth and fusion or joining together of the vertebral bodies 100 and 105 by one or more fusion mechanisms such as osteogenesis, osteoconduction and/or osteoinduction. The graft material may include allograft material, bone graft, bone marrow, a demineralized bone matrix putty or gel and/or any combination thereof. The graft filler material may promote bone growth through and around the substrate apertures 60 and 62 to promote fusion of the intervertebral joint 100 and 105. Those of skill in the art will recognize that the use of filler graft material is optional, and it may or may not be used depending on the needs or requirements of a physician or a medical procedure.

The spinal implant substrate 20 also comprises a first or upper seating area 70 which is comprised of the upper surface periphery of the first and second lateral sidewalls 40 and 50, the leading connector section 35 and rear connector section 55. In the disclosed embodiment, the upper seating area 70 is relatively convexly curved at the lateral side walls 40 and 50 between the leading connector section 35 and rear connector section 55. Those of skill in the art will recognize that other configurations could also be used. The upper seating area 70 includes a leading attachment channel 65 and a rear attachment channel 73 which extend laterally across the implant substrate 20 from the first lateral sidewall 40 to the second lateral side wall 50. The leading and rear attachment channels 65 and 73 further include attachment channel locking portions 64 and 72, respectively, which are physically configured to partially extend over the leading and rear attachment channels 65 and 73 thereby forming the securing or locking mechanism which will lock or secure a securing component 80 or 81 to the implant substrate 20 when the securing component 80 or 81 is attached to the implant substrate 20. The upper seating area 70 is thereby configured and adapted to accept and receive a securing component 80. The securing component 80 can be engaged and locked or substantially secured to the implant substrate upper seating area 70 via complimentary engagement and interaction with the leading and rear attachment channels 65 and 73, for example as shown in FIGS. 2 and 4.

In the preferred aspect, the spinal implant substrate 20 also comprises an opposing second or lower seating area 75 which is comprised of the lower surface periphery of the first and second lateral sidewalls 40 and 50, the leading connector section 35 and rear connector section 55. In a similar manner, the lower seating area 75 is complimentarily configured and adapted to accept and receive a securing component 81 such that the securing component 81 is or can be engaged and locked or substantially secured to the implant substrate lower seating area 75. The lower seating area 75 is substantially convexly curved at the lateral side walls 40 and 50 between the leading connector section 35 and rear connector section 55. The lower seating area 75 includes a leading attachment channel 66 and a rear attachment channel 76 which extend laterally across the lower implant substrate 20 from the first lateral sidewall 40 to the second lateral side wall 50. The leading and rear attachment channels 66 and 76 also include attachment channel locking portions 67 and 77, which are configured to partially extend over the leading and rear attachment channels 66 and 76 thereby forming the securing or locking mechanism which will lock or secure a second lower securing component 81 to the implant substrate 20 when the securing component 81 is attached to the implant substrate 20. The lower seating area 75 is thereby configured and adapted to accept and received a securing component 81. The securing component 81 can be engaged and locked or substantially secured to the implant substrate lower seating area 75 via complimentary engagement and interaction with the leading and rear attachment channels 66 and 76, as shown in FIGS. 2 and 4.

As best shown in FIG. 3, the spinal implant substrate 20 may also one or more comprise securing component positioning openings 68 in the first or second lateral sidewalls 40 and 50. The positioning openings 68 will have a physical configuration complimentary to positioning extensions 88 extending from a securing component 80 or 81. The positioning opening 68 will facilitate the placement of the securing component 80 or 81 onto the implant substrate 20 by permitting entry of the positioning extensions 88 therein, which aligns the securing component 80 or 81 onto the implant substrate 20 as these two components are brought into locking engagement with each other. The positioning openings 68 and the positioning extensions 88 can have a variety of complimentary configuration which permits the placement of the securing component 80 or 81 onto the implant substrate 20. In the preferred aspect, shown in FIG. 3, there are four positioning openings 68 and two pair of corresponding positioning extensions 88.

In the preferred aspect shown in FIGS. 2-5, there are two identical securing components 80 and 81 which respectively attach to opposing upper and lower seating areas 70 and 75. Those of skill in the art will readily recognize that non-identical securing components 80 and 81 may instead be used as may be selected or required by a physician, procedure or medical application. Further, a single securing component 80 or 81 may be used, attached either to the opposing upper and lower seating area 70 and 75, as may be selected or required by a physician, procedure or medical application.

The bone securing component 80 or 81 comprises a leading securing end 82, a rear securing end 84 and bone securing section 90 between the leading securing end 82 and rear securing end 84. The bone securing section 90, in this embodiment, is comprised of first and second component sidewalls 91 and 92 between the leading securing end 82 and rear securing end 84. The leading securing end 82, rear securing end 84 and bone securing section 90 are configured such that they define a securing component aperture 93. The securing component aperture 93 preferably aligns and has a complimentary shape and configuration to the implant substrate aperture 60 as shown in FIGS. 1 and 5. The bone securing component 80 or 81 will permit the upper and lower surfaces of the assembled spinal implant 10 to interact and engage the vertebral endplates 103 and 109 once inserted into the disc space 101, and will prevent the assembled spinal implant 10 from being ejected from the disc space 101 once the spinal implant 10 is positioned in the disc space 101.

The vertebral endplate engagement and anti-ejection aspect of the bone securing component 80 or 81 is provided by a plurality of bone securing component projections, extensions, teeth or serrations 95 which extend outwardly from the bone securing section 90. The bone securing component projections, extensions, teeth or serrations 95 directly interact with and engage the vertebral endplates 103 and 109 when the spinal implant 10 is positioned in the disc space 101 and provide, in part, stability of the implant 10 in the disc space 101 between adjacent vertebrae 100 and 105. In the preferred embodiment, the securing component teeth or serrations 95 are preferably oriented in a rear lean direction such that the securing component teeth or serrations 95 are oriented away or opposite the implant leading end 22 and toward the implant rear end 24. In this manner, the rear leaning orientation of the securing component teeth or serrations 95 provide minimal resistance when the spinal implant is being inserted into a disc space 101. Once inserted, the rear leaning orientation of the securing component teeth or serrations 95 provide a mechanism to prevent the assembled spinal implant 10 from being ejected, or minimize or retard implant movement in a direction tending to eject the implant 10 from the disc space 101, once the spinal implant 10 is positioned in the disc space 101. In the aspect shown in FIGS. 2-4, the teeth 95 are generally triangular in shape when viewed from a side profile. Those of skill in the art will recognize that the bone securing component projections, extensions, teeth or serrations 95 can instead have other shapes, configurations and sizes including, among others, pyramids, triangles, cones, spikes and keels, as well as different teeth orientation, as may be needed or desired by a physician, procedure or medical application.

The bone securing component 80 or 81 also comprises a component seating area 94 opposite or under the component teeth 95 and extending between the leading securing end 82 and rear securing end 84 along the first and second component sidewalls 91 and 92. In the disclosed embodiment, the component seating area 94 is relatively concavely curved between the leading securing end 82 and rear securing end 84. The curved concaveness of the component seating area 94 is preferably configured and shaped such that the component seating area 94 will complimentarily seat on the upper or lower seating area 70 or 75, depending on whether the bone securing component 80 or 81 is being attached to the upper or lower seating area 70 or 75 of the implant substrate 20. Those of skill in the art will recognize that other configurations complimentary shapes and configuration between the component seating area 94 and the upper or lower substrate seating area 70 or 75 can also be used.

The leading securing end 82 also includes a leading attachment extension 83 which extends laterally across the bone securing component 80 or 81 from the first component sidewalls 91 to the second component side wall 92. The opposing rear securing end 84 also includes a rear attachment extension 85 which extends laterally across the bone securing component 80 or 81 from the first component sidewalls 91 to the second component side wall 92. The leading and rear attachment extensions 83 and 85 are configured and adapted to be inserted in the substrate's leading and rear attachment channels 65 and 73. The leading and rear attachment extensions 83 and 85 further include component attachment locking portions 86 and 87, respectively, which are physically configured to extend away from the ends of the leading and rear attachment extensions 83 and 85 thereby forming part of the securing or locking mechanism which will lock or secure the securing component 80 or 81 to the implant substrate 20 when the securing component 80 or 81 is attached to the implant substrate 20.

When the bone securing component 80 or 81 is placed on the implant substrate 20, the component attachment locking portions 86 and 87 enter the corresponding leading and rear substrate attachment channels 65 and 73. The component attachment locking portions 86 and 87 continue travel and begin to deflect or flex such that they permit the bone securing component 80 or 81 to continue to travel into the leading and rear substrate attachment channels 65 and 73. When the component attachment locking portions 86 and 87 travel past the attachment channel locking portions 64 and 72, the attachment locking portions 86 and 87 deflect into the leading and rear substrate attachment channels 65 and 73 thereby mechanically interlocking or lockingly engaging the attachment channel locking portions 64 and 72. At this point, the component attachment locking portions 86 and 87 are interlocked and have lockingly or securely engaged the securing component 80 or 81 to the implant substrate 20 via the attachment channel locking portions 64 and 72. The implant substrate 20 and bone securing components 80 or 81 preferably have complimentary configurations that enable the implant substrate 20 and bone securing components 80 or 81 to interlock in an expedient and convenient assembly process and result in a strong and robust interlocking or locking engagement between the implant substrate 20 and bone securing components 80 or 81. Those of skill in the art will recognize that other locking or interlocking attachment mechanisms may also be used, including among others, pins, rivets, screws, bolts and nuts, adhesive bonding, thermal bonding, mechanical interlocking, over-molding, insert molding, or combination thereof.

As noted previously, the bone securing component 80 or 81 can be securely placed on an upper or lower seating area 70 or 75. The bone securing component 80 or 81 can thus be placed on to the implant substrate 20 such that they are engaged and locked or substantially secured to each other via the complimentary engagement and interaction of the leading and rear attachment extensions 83 and 85 and the respective leading and rear attachment channels 65 and 73, for example as shown in FIGS. 2 and 4. In a preferred embodiment, the securing component 80 or 81 will is placed on the upper or lower seating area 70 or 75 such that securing component 80 or 81 snaps into place when engaged and locked in place on the implant substrate 20. In the configuration of the preferred embodiment 10, the securing component 80 or 81 could instead slide into place in the upper or lower seating area 70 or 75 until it is engaged and locked in place on the implant substrate 20. Those of skill in the art will readily recognize that the manner in which the securing component 80 or 81 attaches and locking engages the implant substrate 20 will depend on the complimentary configurations between the securing component 80 or 81 and the implant substrate 20.

FIGS. 6-9 illustrate a perspective exploded, side and top view of a spinal implant 200 according to another aspect of the present disclosure. This second embodiment is similar to that discussed above with respect to FIGS. 2-5 with the difference that the securing components are now attached to lateral sidewall sections of the implant instead of being attached to upper and lower seating areas. However, in both disclosed embodiments 10 and 200, the bone securing component includes projections, extensions, teeth or serrations that will directly interact with and engage adjacent vertebral endplates 103 and 107 when the spinal implant 10 and 200 is positioned in the disc space 101 and provide stability of the implant 10 and 200 in the disc space 101 between adjacent vertebrae 100 and 105.

The implant 200 comprises an implant body or substrate 220 and first and second securing components 280 and 281 which are attached to the implant body 220. In the embodiment shown in FIGS. 6-9, a first securing component 280 of the spinal implant 10 is secured or attached to an implant's first lateral section or surface 270, and a second securing component 81 is secured or attached to an implant's second lateral section or surface 275. The first and second securing components 280 or 281 are respectively secured or attached to first and second lateral implant sections 270 and 275.

The spinal implant 200 comprises a substrate 220 and at least one bone securing component 280 or 281. The substrate 220 comprises a leading end 222 which has a substantially curved or rounded surface to permit the implant body 200 to distract collapsed or semi-collapsed adjacent vertebral bodies 100 and 105 when the implant 200 is introduced or inserted into a disc space 101. The implant 200 also includes a rear end 224 with a recess section 226 and orifice 228 extending inwardly in a direction from a rear end wall 229 toward the implant's leading end 222. The recess section 226 and orifice 228 provide a means to attach an instrument (not show) to grasp, attach to and manipulate the insertion and orientation of the spinal implant 200 as the implant 200 is delivered to a selected or desired disc space 101. The spinal implant substrate 220 further comprises a substrate connecting or attachment section 230 between the leading and rear end 222 and 224. The substrate attachment section 230 comprises a leading connector section 235 adjacent the leading end 222, a rear connector section 255 adjacent the rear end 224, and first and second lateral sidewalls 240 and 250 between the leading connector section 235 and rear connector section 255. In this embodiment, the first and second lateral sidewalls 240 and 250, the leading connector section 235 and the rear connector section 255 are configured such that they define an implant substrate aperture 260. The present embodiment further includes first and second lateral wall substrate apertures 262. The implant apertures 260 and 262 permit the insertion of a graft material which assists in promoting fusion 100 and 105 of the adjacent vertebrae at the disc space 101 where the implant 10 is inserted.

Figure 6:
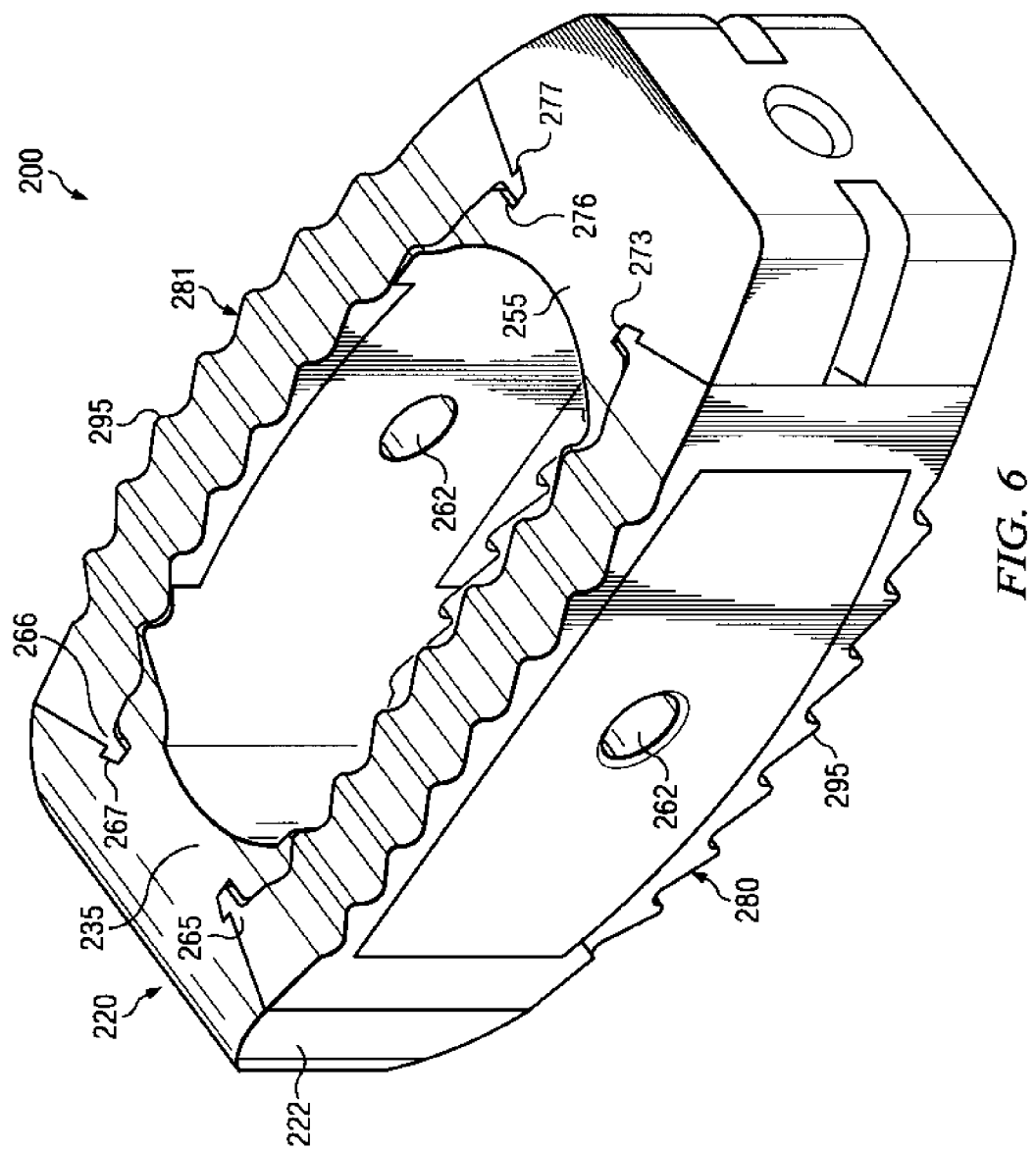
FIG. 6 is a perspective view of an implant according to another embodiment of the present disclosure.
Figure 7:
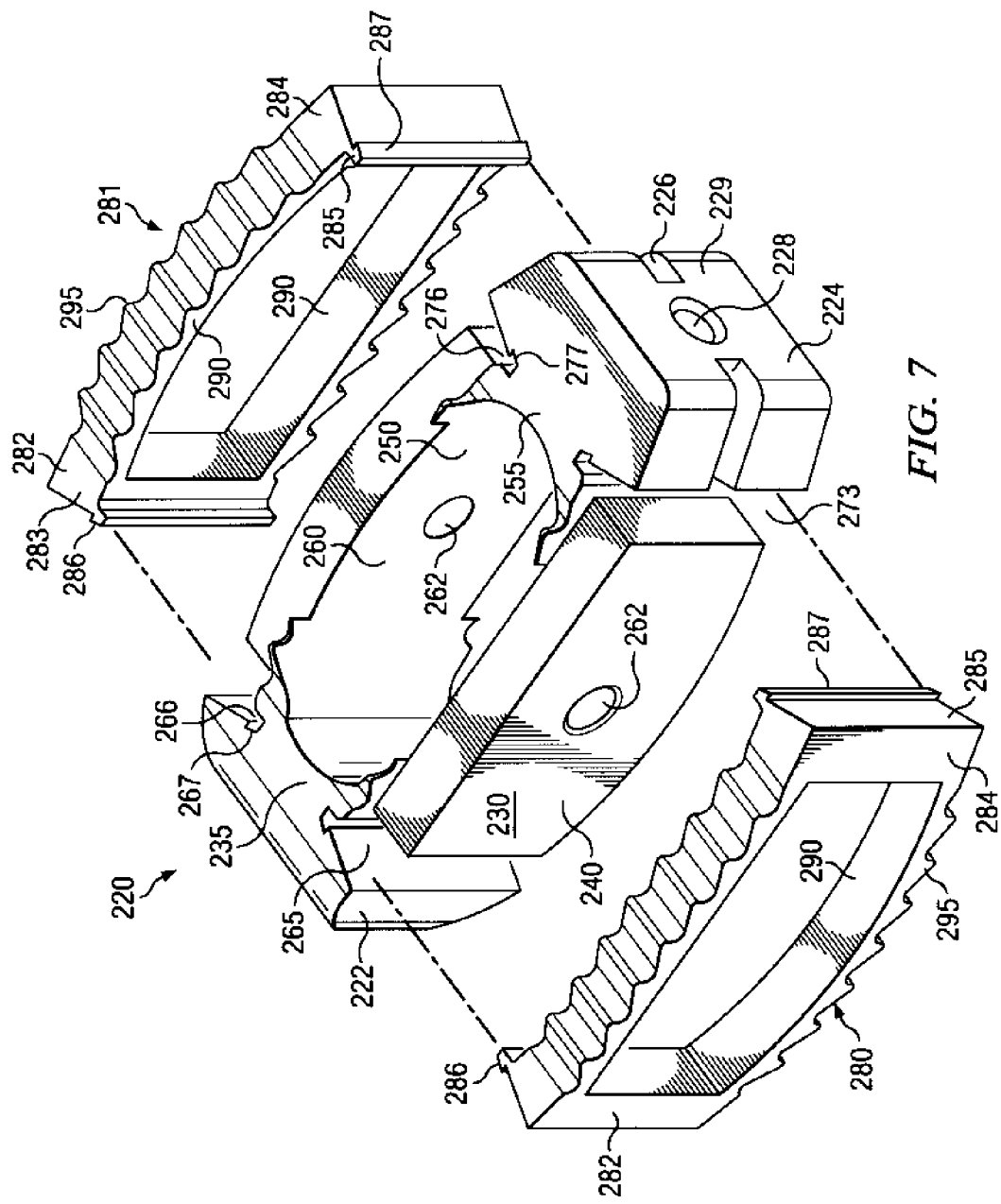
FIG. 7 is an exploded perspective view of the implant of FIG. 6.
Figure 9:
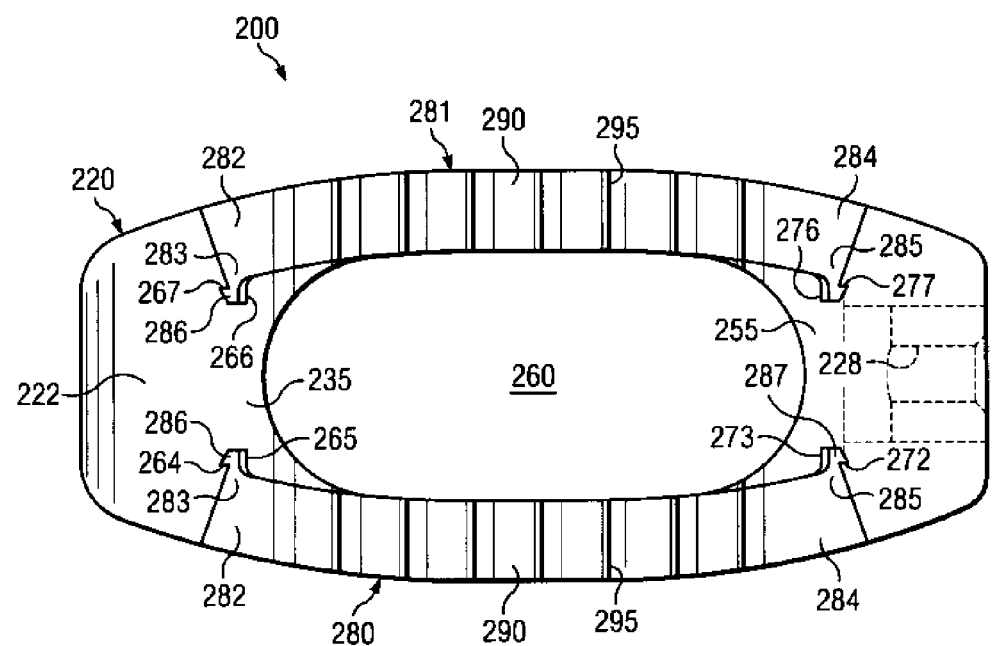
FIG. 9 is a top view of the implant of FIG. 6.

The spinal implant substrate 220 also comprises a leading attachment channel 265 and a rear attachment channel 273 which extend across and along the first lateral sidewall 240 from an upper to a lower portion of the lateral sidewall 240. The leading and rear attachment channels 265 and 273 further include attachment channel locking portions 264 and 272, respectively, which are physically configured to partially extend over the leading and rear attachment channels 265 and 273 thereby forming the securing or locking mechanism which will lock or secure a securing component 280 to the implant substrate 220 when the securing component 280 or 281 is attached to the implant substrate 220. The first lateral sidewall 240 is thereby configured and adapted to accept and receive a securing component 280. The securing component 280 can be engaged and locked or substantially secured to the first lateral sidewall 240 via complimentary engagement and interaction with the leading and rear attachment channels 265 and 273, as shown in FIGS. 6, and 9.

In a similar manner, the second lateral sidewall 250 is complimentarily configured and adapted to accept and receive a securing component 281 such that the securing component 281 is or can be engaged and locked or substantially secured to the second lateral sidewall 250. The spinal implant substrate 220 comprises a second leading attachment channel 266 and a rear attachment channel 276 which extend across and along the second lateral sidewall 250 from an upper to a lower portion of the second lateral sidewall 250. The leading and rear attachment channels 266 and 276 further include attachment channel locking portions 267 and 277, respectively, which are physically configured to partially extend over the leading and rear attachment channels 266 and 277 thereby forming the securing or locking mechanism which will lock or secure a securing component 281 to the implant substrate 220 when the securing component 281 is attached to the implant substrate 220. The second lateral sidewall 250 is thereby configured and adapted to accept and receive a securing component 281. The securing component 281 can be engaged and locked or substantially secured to the second lateral sidewall 250 via complimentary engagement and interaction with the leading and rear attachment channels 266 and 276, as shown in FIGS. 6, and 9.

In the embodiment shown in shown in FIGS. 6-9, there are two identical securing components 280 and 281 which respectively attach to opposing lateral sidewalls 240 and 250. Those of skill in the art will recognize that non-identical securing components 280 and 281 may instead be used as may be selected or required by a physician, procedure or medical application sol long as they are lockingly complimentary to their respective lateral sidewall 240 and 250. Further, a single securing component 280 or 281 may be used, attached either to the opposing lateral sidewall 240 or 250, as may be selected or required by a physician, procedure or medical application. The bone securing component 280 or 281 comprises a leading securing end 282 and a rear securing end 284 and a bone securing section 290 between the leading securing end 282 and rear securing end 284. The bone securing section 290, in this embodiment, is comprised of first and second component walls 291 and 292 between the leading securing end 282 and rear securing end 284. The bone securing component 280 or 281 will permit the upper and lower surfaces of the assembled spinal implant 200 to interact and engage the vertebral endplates 103 and 109 once inserted into the disc space 101, and will prevent the assembled spinal implant 200 from being ejected from the disc space 101 once the spinal implant 200 is positioned in the disc space 101.

The vertebral endplate engagement and anti-ejection aspect of the bone securing component 280 or 281 is provided by a plurality of bone securing component projections, extensions, teeth or serrations 295 which extend outwardly from the bone securing section 290. The bone securing component teeth 295 directly interact with and engage the vertebral endplates 103 and 109 when the spinal implant 200 is positioned in the disc space 101 and provide stability of the implant 200 in the disc space 101 between adjacent vertebrae 100 and 105. In this embodiment, the securing component teeth 295 are preferably oriented in a rear lean direction such that the securing component teeth 295 are oriented away or opposite the implant leading end 222 and toward the implant rear end 224. In this manner, the rear leaning orientation of the securing component teeth 295 provide minimal resistance when the spinal implant is being inserted into a disc space 101. Once inserted, the rear leaning orientation of the securing component teeth or serrations 295 provide a mechanism to prevent the assembled spinal implant 200 from being ejected, or minimize or retard implant movement in a direction tending to eject the implant 10 from the disc space 101, once the spinal implant 200 is positioned in the disc space 101. In the aspect shown in FIGS. 6-9, the teeth 295 are generally triangular in shape when viewed from a side profile. Those of skill in the art will recognize that the bone securing component projections, extensions, teeth or serrations 295 can instead have other shapes, configurations and sizes including, among others, pyramids, triangles, cones, spikes and keels, as well as different teeth orientation, as may be needed or desired by a physician, procedure or medical application.

The leading securing end 282 also includes a leading attachment extension 283 which extends across and along the leading securing end 282 from an upper to a lower portion of the leading securing end 282. The opposing rear securing end 284 also includes a leading attachment extension 285 which extends across and along the rear securing end 284 from an upper to a lower portion of the rear securing end 284. The leading and rear attachment extensions 283 and 285 are configured and adapted to be inserted in the substrate's leading and rear attachment channels 265 and 273. The leading and rear attachment extensions 283 and 285 further include component attachment locking portions 286 and 287, respectively, which are physically configured to extend away from the ends of the leading and rear attachment extensions 283 and 285 thereby forming part of the securing or locking mechanism which will lock or secure the securing component 280 or 281 to the implant substrate 220 when the securing component 280 or 281 is attached to the implant substrate 220. The implant substrate 220 and bone securing components 280 or 281 preferably have complimentary configurations that enable the implant substrate 220 and bone securing components 280 or 281 to interlock in an expedient and convenient manner and result in a strong locking engagement between the implant substrate 220 and bone securing components 280 or 281. Those of skill in the art will recognize that other locking or interlocking attachment mechanisms may also be used, including among others, pins, rivets, screws, bolts and nuts, adhesive bonding, thermal bonding, mechanical interlocking, over-molding, insert molding, or combination thereof.

When the bone securing component 280 or 281 is placed on the implant substrate 220, the component attachment locking portions 286 and 287 enter the corresponding leading and rear substrate attachment channels 225 and 273. The component attachment locking portions 286 and 287 continue travel and begin to deflect or flex such that they permit the bone securing component 280 or 281 to continue to travel into the leading and rear substrate attachment channels 265 and 273. When the component attachment locking portions 286 and 287 travel past the attachment channel locking portions 264 and 272, the attachment locking portions 286 and 287 deflect into the leading and rear substrate attachment channels 265 and 273 thereby lockingly engaging the attachment channel locking portions 264 and 272. At this point, the component attachment locking portions 286 and 287 have lockingly or securely engaged the securing component 280 or 281 to the implant substrate 220 via the attachment channel locking portions 264 and 272.

Figure 8:
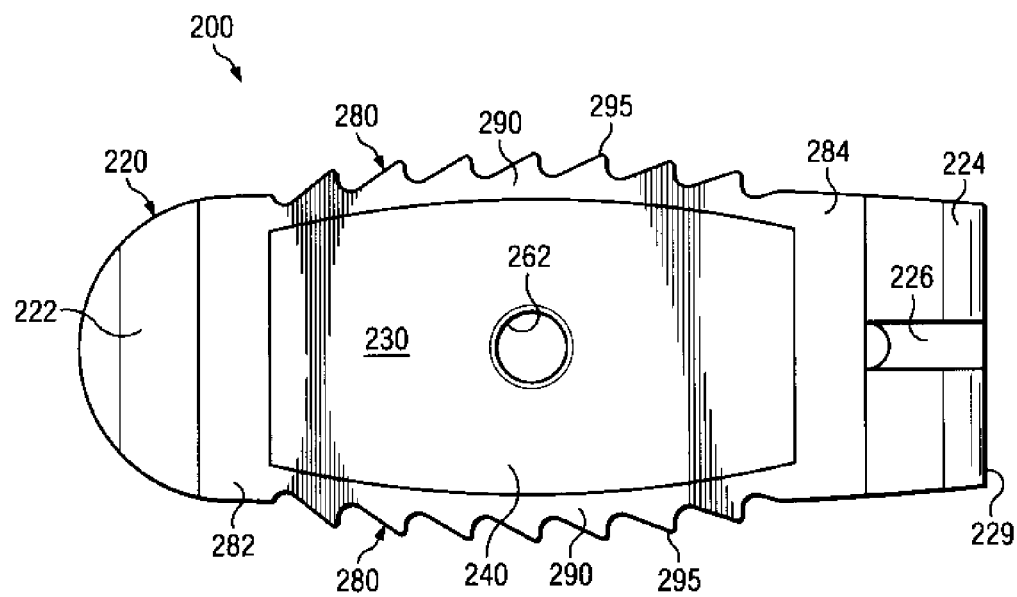
FIG. 8 is a side view of the implant of FIG. 6.

As noted previously, the bone securing component 280 or 281 can be securely placed on first and second lateral sidewalls 240 and 250. The bone securing component 280 or 281 can thus be placed on to the implant substrate 220 such that they are engaged and locked or substantially secured to each other via the complimentary engagement and interaction of the leading and rear attachment extensions 283 and 285 and the respective leading and rear attachment channels 265 and 273, for example as shown in FIGS. 6 and 8-9. In this embodiment, the securing component 280 or 281 is placed on the first and second lateral sidewalls 240 and 250 such that it snaps into place when engaged and locked in place on the implant substrate 220. In this configuration, the securing component 280 or 281 could instead slide into place in the first and second lateral sidewalls 240 and 250 until the securing component 280 and 281 is engaged and locked in place on the implant substrate 220. Those of skill in the art will readily recognize that the manner in which the securing component 280 or 281 attaches and locking engages the implant substrate 220 will depend on the complimentary configurations between the securing component 280 or 281 and the implant substrate 220.

In the disclosed embodiment of FIGS. 2-5, a spinal implant, commercialized by Medtronic, Inc, under the trademark CLYDESDALE®, is contemplated as using and embodying the advantageous aspects of the spinal implant 10 disclosed herein. Those of skill in the art will readily recognize that other implant sizes and configuration designs may use or incorporate the advantageous aspects of the spinal implant 10 disclosed herein. This includes implants having different leading end and rear end configurations. For example, the unique and advantageous aspects of the spinal implant 10 disclosed herein may be implemented and used in others spinal implants commercialized by a third party, including spinal implant commercialized by Medtronic, Inc, under the trademarks CAPSTONE®, CRESCENT®, etc., along with associated or corresponding delivery and insertion implant instruments. Those of skill in the art will further recognize that implant 10 could also comprise a substrate 20 and securing component 80 or 81 with resultant implant walls which are angled relative to one another so as to achieve a desired or selected kyphosis, lordosis, or lateral wedge effect when inserted in the disc space 101. In other embodiments, an implant wall or surface may extend obliquely from an adjacent wall rather than orthogonally. Also, an implant's walls could be tapered, sloped, angled, or curved, including covex, bi-convex and concave curving, depending on a particular medical application need or requirement.

The spinal implants 10 and 200 disclosed in this disclosure are preferably comprised of a biocompatible radiolucent implant substrate with an attachable biocompatible radiopaque and osseoconductive securing component which is configured and adapted for insertion into and positioning in an intervertebral disc space so as to contact against adjacent vertebral members. The biocompatible implant substrate 20 and 220 is preferably a polyetheretherketone (PEEK) polymer material. The spinal implant 10 and 200 contemplated herein allows radiographic assessment of fusion and the bridging bone mass across the disc space while reducing stress-shielding effects. The securing components 80, 81, 280 and 281 includes a bone securing section 90 and 290 with an appropriate surface texture that can include serrations or teeth 95 and 295 which provide or promote fixation as well as long-term osseointegration for the device while allowing assessment of osseointegration between vertebral endplates and spinal implant surfaces. Fusion and osseointegration can be improved and accelerated through the use and application of a Hydroxyapatite or HA coating on the bone-contacting side of the securing component 90 and 290.

The implant substrate 20 and 220 is preferably a radiolucent biocompatible materials such as PEEK and carbon fiber reinforced PEEK, etc., however, those of skill in the art will recognize that other substrate material may also be used, including among others, polymer material, homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyetherketoneketone (PEKK); polyaryletherketones (PAEK), cellulose, carbon fiber reinforced composite, and mixtures thereof.

The biocompatible radiopaque and osseoconductive securing component 10 and 200 is preferably a Titanium (Ti) metallic material. However, those of skill in the art will recognize that other metallic materials may also be used, including, among others, stainless steel, titanium alloys, nitinol, platinum, tungsten, silver, palladium, gold, cobalt chrome alloys, shape memory nitinol and mixtures thereof. Additionally, the metallic material may have a porosity aspect in order to improve fixation of the implant. The bone-contacting surfaces of the securing component's metallic material may have porosity of appropriate or desired sizes and geometry or configuration for optimal and rapid bony in growth. The securing component's porosity may have pores that are non-connected or interconnected pores with pore size diameter in the range between 1 to 1000 micrometers, preferably between 50 and 250 micrometers. The porosity may have predetermined patterns or have a porosity that has a random geometry or configuration in nature. The porosity can be further coated or filled with osseoconductive and/or osseoinductive biomaterials such as hydroxyapatite (HA) and human recombinant bone morphogenic protein (rh BMP2). Those of skill in the art will recognize that the pore sizes, pore configuration, pore coating, and/or pore inter-connectivity aspect may be selected or vary for a particular spinal implant 10 or 200 depending on needs or requirements of a physician, procedure or medical application. Further, the biocompatible substrate 20 and 200 and securing components 90 and 290 used may depend on the patient's need and physician requirements. The spinal implant substrate 20 and 220 and bone securing component 90 and 290 can be made or manufactured by typical or known techniques and methods know to those of skill in the art, including among others, machining, molding, extrusion, stamping, laser processing, water-jet cutting or combination thereof.

The implant 10 or 200 may be implanted in the disc space 101 using known methods, procedures and approaches, including a posterior (PLIF), direct lateral (DLIF), anterior (ALIF), translateral (TLIF) or any other suitable oblique direction and approach, as those of skill in the art will recognize. Further, a spinal implant may be delivered and inserted through known surgical technique and procedures, including: open, mini-open, minimal access spinal technologies (MAST) or other minimally invasive surgical (MIS) techniques.

In one approach, the implant 10 or 200 is inserted via a posterior (PLIF) approach, for example as shown in FIG. 1. In one aspect, the implant 10 or 200, shown in FIGS. 2 and 6, will have a selected or desired physical shape and size for use in a spinal medical procedure. Those of skill in the art will readily recognize that the implant 10 or 200 may take on any shaped desired or required for a particular medical use or application. Further, those of skill in the art will recognize that the implant can also be a dynamic vertebral implant device, with varying shape and size depending on the medical application where the implant used.

Prior to insertion, known medical instruments and tools may be used to prepare the intervertebral disc space 101, including pituitary rongeurs and curettes for reaching the nucleus pulposus or other area in the disc space 101. The disc space 101 may be prepared with a partial or complete discectomy. Ring curettes may be used as necessary to scrape abrasions from the vertebral endplates 103 and 107. Using such instruments, a location which will accept the implant 10 or 200 is prepared in the disc space 101. Those of skill in the art will recognize that the implant 10 or 200 may be positioned at any desired location between the adjacent vertebral bodies 103 and 107 depending on the surgeon's need and the performed surgical procedure or medical application.

The implant is then inserted into the prepared disc space 101 using insertion instruments which are appropriate with the shape and configuration of the implant and surgical procedure to be used. A medical imaging technique and device may be used to visualize the implant 10 or 200 during the insertion procedure by taking advantage of the implant's radiolucent and radiopaque properties. During the insertion step, the enhanced implant visualization will permit the surgeon to better maneuver and control the trajectory, position and orientation of the implant 10 or 200 into the vertebral disc space 101 and through the surrounding patient anatomical environment.

The implant 10 or 200 is then delivered into the intervertebral disc space 101 and positioned in a selected location and orientation between the end plates 103 and 107 of the adjacent vertebral bodies 100 and 105. The implant is inserted into the disc space 101 such that the upper securing component 80 and/or 81 is positioned adjacent to the upper vertebral endplate 103 and the lower securing component 80 and/or 81 is positioned adjacent to the lower vertebral endplate 107. The teeth projections 95 may engage the vertebral endplates 103 and 107 to provide stability to the implant 10 or 200. Once implanted, the upper securing components 80 and/or 81 will contact the upper vertebral end plate 103 to form an interface between the implant 10 or 200 and the upper vertebral body 100. Also, the lower securing component 81 will contact the lower vertebral end plate 107 to form an interface between the implant 10 or 200 and the lower vertebral body 105. After the insertion of the implant 10 or 100 between the vertebral bodies 100 and 105 has been completed, the implant 10 or 200 graft material will promote the fusion or joining together of the vertebral bodies 100 and 105.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

While embodiments of the invention have been illustrated and described in detail in the present disclosure, the disclosure is to be considered as illustrative and not restrictive in character.

While embodiments of the invention have been illustrated and described in the present disclosure, the disclosure is to be considered as illustrative and not restrictive in character. The present invention may be carried out in other specific ways than those herein set forth without departing from the scope and essential characteristics of the invention. The present embodiments are, therefore, to be considered in all respects as illustrative and not restrictive, and all changes and modifications that come within the spirit of the invention are desired to be protected and are to be considered within the scope of the disclosure. Further, all changes coming within the meaning and equivalency range of the appended claims are also intended to be embraced therein.

The invention claimed is:

1. A spinal implant for insertion into and positioning in an intervertebral disc space, the implant comprising:
    an implant substrate extending along a longitudinal axis between a leading end and a rear end, the implant substrate comprising at least one attachment aspect and a recessed intermediate portion between the leading and rear ends comprising first and second faces extending transverse to the longitudinal axis; and
    a securing component comprising at least one securing aspect, a first end and a second end, the securing component being positioned within the intermediate portion such that the first end engages the first face and the second end engages the second face;
    wherein the attachment aspect engages the securing aspect to couple the securing component to the implant substrate.

2. The implant of claim 1, wherein the securing component comprises a plurality of extensions adapted to engage adjacent vertebrae when the implant is in positioned in the disc space.

3. The implant of claim 2, wherein the securing component further comprises an Hydroxyapatite (HA) layer.

4. The implant of claim 1, wherein the intermediate portion is positioned at an upper or lower implant section of the implant substrate.

5. The implant of claim 1, wherein the intermediate portion is positioned at a lateral implant section of the implant substrate.

6. The implant of claim 1, wherein
the implant substrate is comprised of a radiolucent material; and
the securing component is comprise of a radiopaque material.

7. The implant of claim 1, wherein the securing aspect and the attachment aspect have a mechanical interlocking configuration.

8. The implant of claim 1, wherein the implant substrate is polyetheretherketone (PEEK).

9. The implant of claim 1, wherein the implant substrate is carbon fiber reinforced polyetheretherketone (PEEK).

10. The implant of claim 1, wherein the securing component is a metallic material.

11. The implant of claim 10, wherein the metallic material is porous.

12. The implant of claim 10, wherein the metallic material is titanium (Ti) or a titanium (Ti) alloy.

13. A spinal implant for insertion into and positioning in an intervertebral disc space, the implant comprising:
a radiolucent implant substrate extending along a longitudinal axis between a leading end and a rear end, the implant substrate comprising at least one attachment aspect and a recessed intermediate portion between the leading and rear ends comprising first and second faces extending transverse to the longitudinal axis;
a radiopaque securing component comprising at least one securing aspect, a plurality of extensions, a first end and a second end, the securing component being positioned within the intermediate portion such that the first end engages the first face and the second end engages the second face;
wherein the attachment aspect engages the securing aspect to couple the securing component to the implant substrate; and
wherein the plurality of extensions are adapted to engage adjacent vertebrae when the implant is in positioned in the disc space.

14. The implant of claim 13, wherein the intermediate portion is positioned at an upper or lower implant section of the implant substrate.

15. The implant of claim 13, wherein the intermediate portion is positioned at a lateral implant section of the implant substrate.

16. The implant of claim 13, wherein the securing aspect and the attachment aspect have a mechanical interlocking configuration.

17. The implant of claim 13, wherein the implant substrate is polyetheretherketone (PEEK).

18. The implant of claim 13, wherein the securing component is a metallic material which is porous.

19. The implant of claim 18, wherein the metallic material is titanium (Ti) or a titanium (Ti) alloy.

20. The implant of claim 13, wherein the securing component further comprises an Hydroxyapatite (HA) layer.

* * * * *